United States Patent [19]

Dassler et al.

[11] Patent Number: 5,331,174
[45] Date of Patent: Jul. 19, 1994

[54] METHOD OF INSPECTING THE DIMENSIONAL ACCURACY OF MEDICAL AMPULS

[75] Inventors: Hans-Ulrich Dassler, Oberschleissheim; Rüdiger Haas, Faistenhaar; Johann Lang, Oberschleissheim, all of Fed. Rep. of Germany

[73] Assignee: Schott Glaswerke, Mainz, Fed. Rep. of Germany

[21] Appl. No.: 969,218

[22] PCT Filed: Apr. 3, 1992

[86] PCT No.: PCT/EP92/00755
§ 371 Date: Feb. 5, 1993
§ 102(e) Date: Feb. 5, 1993

[87] PCT Pub. No.: WO92/17770
PCT Pub. Date: Oct. 15, 1992

[30] Foreign Application Priority Data
Apr. 6, 1991 [DE] Fed. Rep. of Germany ....... 4111145

[51] Int. Cl.⁵ ............................................. G01N 21/86
[52] U.S. Cl. .................................. 250/560; 250/223 B
[58] Field of Search ........................... 250/560, 223 B; 356/239, 240, 384, 385, 386, 387; 358/107

[56] References Cited

U.S. PATENT DOCUMENTS 2,857,038 10/1958 Noble et al. .
3,458,967 8/1969 Ziche .
4,367,405 1/1983 Ford .................................. 250/223 B
4,483,615 11/1984 Bieringer et al. .
4,549,205 10/1985 Misaki et al. .................... 250/223 B
4,725,856 2/1988 Fujikura ............................. 356/240
4,731,649 3/1988 Chang et al. .
4,912,318 3/1990 Kajiura et al. ................... 250/223 B
4,975,568 12/1990 Taniguchi et al. .

FOREIGN PATENT DOCUMENTS 0387930 9/1990 European Pat. Off. .
55-76942 6/1980 Japan .

Primary Examiner—David C. Nelms
Attorney, Agent, or Firm—Spencer, Frank & Schneider

[57] ABSTRACT

To automatically examine medical ampuls to determine their dimensional accuracy, the ampuls are moved in a horizontal position on a chain conveyor in a cadenced manner through an optoelectronic testing station. At the testing station, each ampul is lifted out of the chain conveyor and illuminated by light from a diffusely radiating illumination source perpendicularly to the longitudinal axis of the ampul. In the case of one-point-cut ampuls, the ampuls are rotated about their longitudinal axes during the testing process. The light passing through the ampul is received by a photodiode camera system which converts the images into electrical image signals. These image signals are evaluated with respect to their changes in intensity produced by the tested ampul in order to generate measurement values for the desired ampul dimensions and, if applicable, for their deviations from standard ampul dimensions.

21 Claims, 9 Drawing Sheets

METHOD OF INSPECTING THE DIMENSIONAL ACCURACY OF MEDICAL AMPULS

BACKGROUND OF THE INVENTION

The invention relates to a method for inspecting medical ampuls for dimensional accuracy, wherein the ampuls are held in a horizontal position on a conveying device and are moved in cycles through an inspection station.

Medical ampuls must meet high demands for dimensional accuracy since the quantity filled into them is not measured when the ampuls are filled. Instead, it is assumed that if they are filled to a predetermined fill marker the desired fill level is accurately attained. The fill quantities are generally relatively small, so small dimensional fluctuations signify relatively great changes in the fill quantity. This leads to a correspondingly great fluctuation in the pharmacologically effective dosage for administration of the medications packaged in the ampuls.

SUMMARY OF THE INVENTION

It is the object of the invention to check the dimensional accuracy of medical ampuls automatically and without contact.

According to the invention, accomplished by a method in which:

(a) during the transporting intervals, each ampul is lifted out of its support for inspection and is illuminated by transmitted light from a diffusely radiating illumination source perpendicularly to its longitudinal axis, with the ampul to be examined being rotated about its longitudinal axis if required;

(b) the light passing through each ampul is modulated in its brightness by the variations in geometry and/or transparency, with this brightness modulation constituting optical information about the measuring parameters;

(c) the modulated light is directed into the beam path of a camera system equipped with photodiodes;

(d) the photodiodes of the camera system produce an image of the outline of the ampul or— in the case where the ampul being examined is rotated about its longitudinal axis— of a sequence of individual surface strips of the ampul being examined corresponding to a development of the ampul surface; and (e) the resulting images are transmitted as electrical image signals to a digital image evaluation unit and are there evaluated with respect to their brightness modulation to the extent that measurement values are generated for the desired ampul dimensions and, if applicable, for their deviations from standard ampul dimension.

The invention is based on the concept of scanning each ampul opto-electronically and digitally evaluating the scanned values. In dependence on the determined dimensional accuracy, the respective ampuls can be positively separated without interruption of production if a fixed tolerance range is exceeded so that the production of rejects can be determined accurately. Additionally, the practically delay-free checking of all ampuls when exceeded tolerances are detected permits immediate access to the tools that produce the medical ampuls, so that production of rejects can be quickly detected and eliminated. With the aid of digital evaluation it is also possible to compile a complete measuring protocol for all ampuls of each production charge as a proof of quality for the purchasers of the ampuls. Moreover, the precision of the manufacturing tools and their service life can also be checked with the aid of the compiled measuring protocols.

BRIEF DESCRIPTION OF THE DRAWINGS

The invention will now be described in greater detail with reference to embodiments thereof that are illustrated in the drawings, in which.

DESCRIPTION OF THE PREFERRED EMBODIMENTS

Figure 1A:
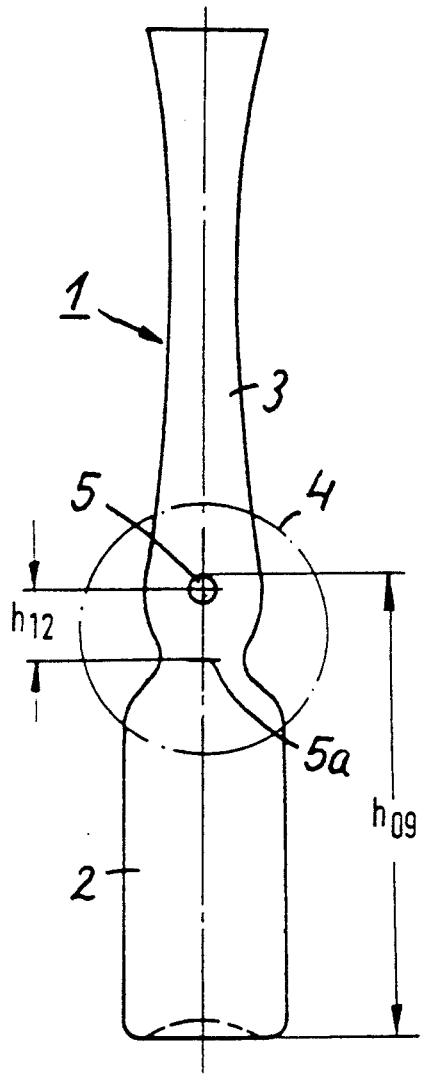
FIG. 1A is a view of a so-called one-point-cut (OPC) ampul in the empty state in which the axially symmetrical position of a colored marker and the position of a scratch mark serving as an intended break location relative to the colored marker constitute special inspection parameters in addition to the outline dimensions of the ampul.
Figure 1B:
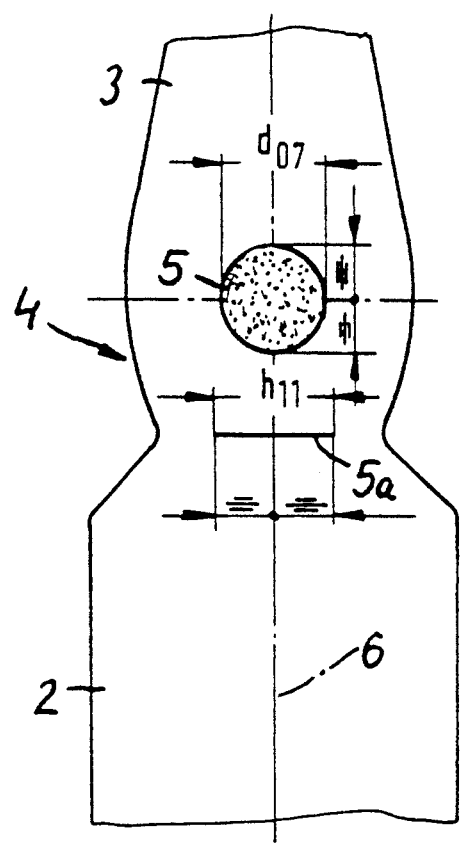
FIG. 1B is a detail view of the OPC ampul of FIG. 1a in the region of the colored marker.
Figure 2C:
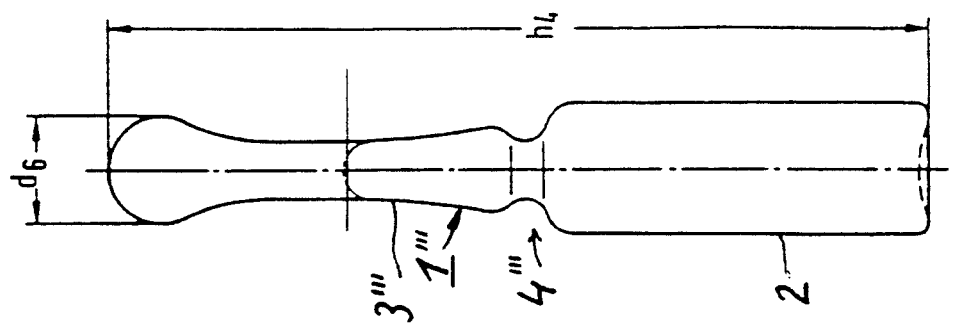
FIGS. 2A, 2B, and 2C are views of various ampul shapes according to DIN [German Industrial Standard] 58,377 to illustrate the outline dimensions to be examined.

The method according to the invention is employed to check medical ampuls for dimensional accuracy. For better understanding, different shapes and embodiments of ampuls are illustrated in FIGS. 1A and 1B. The ampul 1 of FIG. 1 is a so-called one-point-cut (OPC) ampul which is composed of a cylindrical body 2 and a more slender neck section (lance, funnel) 3. The transition region (bulb) 4 between the body 2 and the neck section 3 has a constriction that is characteristic for all medical ampuls. When the filled ampul is put to use, the neck section 3 is broken off at this transition region 4. FIGS. 2A and 2C respectively show a lance ampul 1' having a body 2, a neck section 3', and a transition region 4', a funnel ampul 1'' having a body 2, a neck section 3'', and a transition region 4'', and a burn-open ampul 1''' having a body 2, a neck section 3''', and a transition region 4'''. A scratch mark is made with a rasp in the transition region of the ampuls shown in FIGS. 2A to 2C. The neck section which acts as a relatively long lever arm, is bent toward body 2 to break the neck section off. In the OPC ampul of FIG. 1, such a scratch mark is already provided during the manufacturing process as the intended break location 5a so that this type of ampul is ready for use without any prior rasping. Since the intended break location 5a is produced by machine and is difficult to see with the naked eye when the ampul 1 is full, the OPC ampul of FIG. 1 is provided with a colored marker 5 above the intended break location 5a. The marker 5 is precisely centered, as shown in FIG. 1B, on the longitudinal axis 6 of the ampul. Furthermore the marker 5 has a fixed diameter, a fixed height with respect to the bottom of the ampul and a fixed axial distance from the intended break location 5a. The intended break location 5a also has a defined length. All of these features are standard and must be covered during inspection of an OPC ampul in addition to the dimensional accuracy of its outline. The same also applies for the remaining ampul dimensions identified in FIGS. 2A-2C and corresponding to DIN standard DIN 58,377.

Figure 2B:
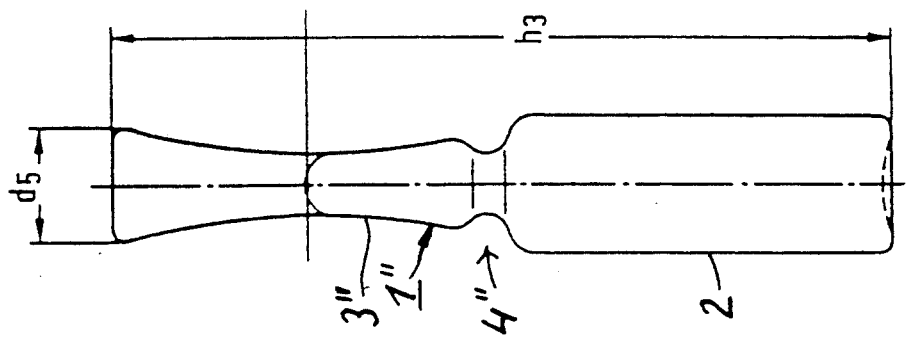
Figure 2A:
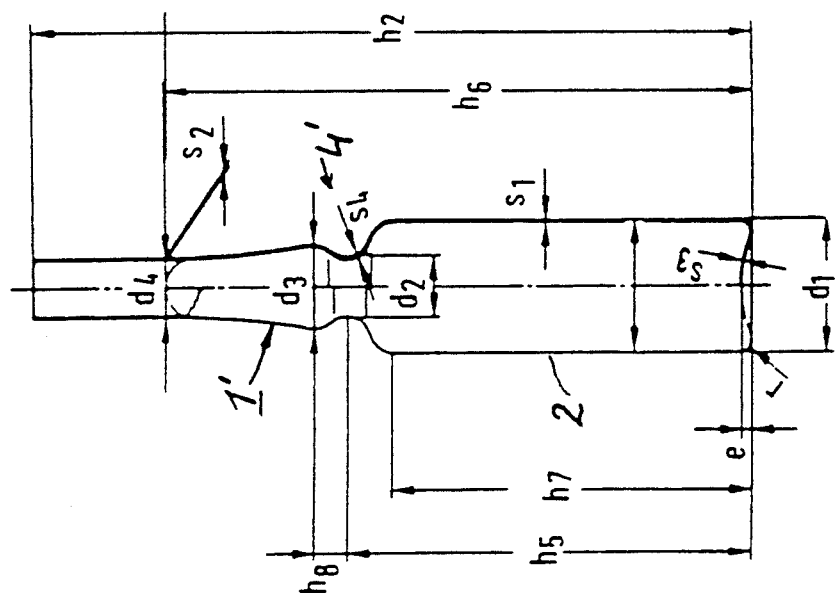
Figure 3:
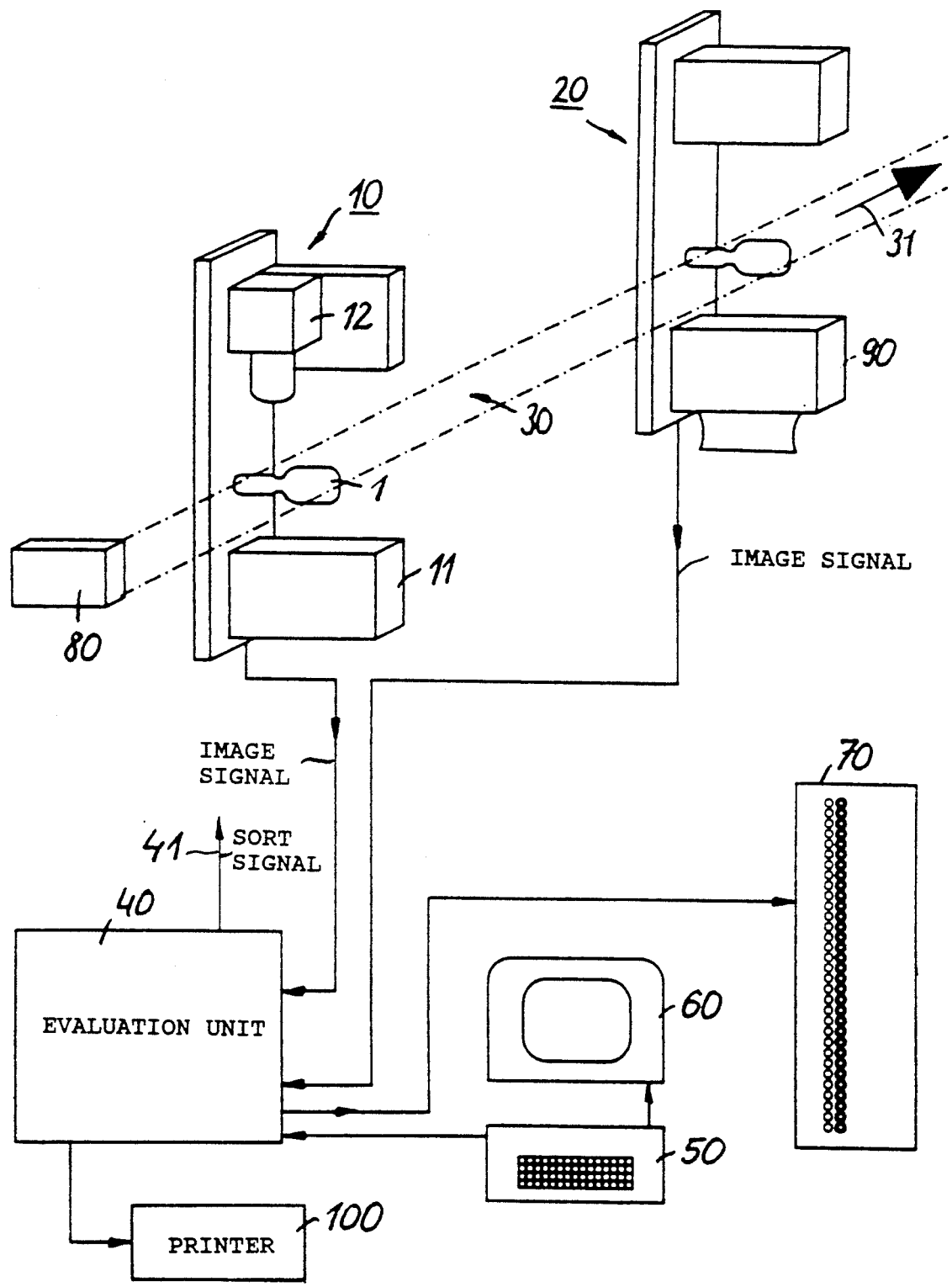
FIG. 3 is a schematic representation of a device composed of two inspection stations for implementing the method according to the invention.

The special features (the colored dot 5, scratch mark 5a, and constriction or break ring) of an OPC ampul as shown in FIG. 1 are measured with respect to their geometry with the aid of an opto-electronic inspection station 10 without contact on each produced ampul, while the outline dimensions of the various ampul shapes shown in FIGS. 2A-2C are detected by an automatic outline inspection performed with the aid of an opto-electronic inspection station 20 (FIG. 3). The outline inspection also permits an examination for the existence of glass fragments. The device for implementing the method according to the invention shown in FIG. 3 includes a chain conveyor 30 for supplying the two inspection stations 10 and 20 on which the ampuls 1 lie in a horizontal, that is, prone position and move through inspection stations 10 and 20 in direction of the arrow 31.

For each individual ampul each inspection station produces an electrical image signal which is fed to an evaluation unit 40. The evaluation unit 40 also receives, by way of a terminal composed of a keyboard 50 and a monitor 60, desired value data for the dimensions of the ampuls examined in inspection stations 10 and 20. From the image signals supplied to it, evaluation unit 40 determines the various ampul dimensions according to FIGS. 1 and 2A-2C, compares the determined dimensions with the put-in desired values, and sets up and prints out by way of a printer 100 a measuring protocol for each inspected ampul. In addition, the evaluation unit controls a display board 70 where a red and a green signal lamp are provided for each individual inspection parameter. As long as the measured value for a certain parameter lies within the tolerance range, the green lamp lights up, while the red lamp for the respective parameter lights up on the display board when a tolerance range is exceeded. In this way, the operating personnel are able to determine at a glance whether and, if so, which parameters lie outside of the standard. Another output 41 of evaluation unit 40 is charged with a sorting signal if evaluation unit 40 determines that an inspected ampul is not usable. In a non-illustrated sorting unit the sorting signal initiates the removal of the respective ampul from chain conveyor 30. In this way, rejects can be positively removed from the production line. The removal of an ampul is noted in the measuring protocol.

As shown in FIG. 3, the opto-electronic inspection station 10 for checking OPC ampuls according to FIG. 1 includes a diffusely radiating illumination source 11 disposed below chain conveyor 30. Due to its variations in transparency, the ampul 1, which moves in a horizontal position through the diffuse beam path of illumination source 11, produces a brightness and intensity modulation of the diffuse light passing through its glass body, with this brightness and intensity modulation constituting optical information. The variations in transparency are produced by the colored marker 5, the intended break location 5a in the form of a scratch mark and by the-non-illustrated break ring. In this connection it is important, in order to avoid distortions and thus measuring errors, that the diffuse light beams from illumination source 11 extend perpendicularly to the longitudinal axis of ampul 1.

The modulated beams that have passed through the glass body of ampul 1 directly enter, that is, without any deflection, the beam path of a camera system 12. Camera system 12 essentially included an optical system 12a (see FIG. 6) as well as an array of photodiodes as the opto-electronic image converter. Such photodiode cameras have the advantage of high resolution and an accurate space-time relationship between the position of each photodiode within the array and the intensity pulses originating from the individual photodiodes within the image signal. In order to avoid imaging errors, the photodiode array is oriented exactly parallel to the longitudinal axis of ampul 1 and exactly perpendicular to the beam path of the light passing through ampul 1. Since the photodiode array at that moment furnishes an image of only a narrow strip of the surface of ampul 1 parallel to its longitudinal axis, it is necessary, in order to detect the colored marker 5 and the intended break location 5a, which is also provided only over a small portion of the circumference of the ampul, to produce a development of the entire ampul surface. For this purpose, ampul 1 is rotated during its illumination by 360° about its longitudinal axis with the aid of a friction wheel 16 shown in detail in FIG. 6, with the sequence of surface strips recorded by the photodiode camera system 12 being combined by evaluation unit 40 into a development of the surface. The complete rotation of ampul 1 about its longitudinal axis is made possible by the cyclic operation of the chain conveyor 30 provided in any case. During each stopped phase of chain conveyor 30, a lifter remover 80 (see FIGS. 3 and 4) provided in inspection station 10 lifts ampul 1 from its support on chain conveyor 30 toward friction wheel 16 in the direction of photodiode camera system 12 until the ampul 1 has revolved once around its longitudinal axis. Then lifter remover 80 returns the examined ampul 1 back into its support on chain conveyor 30, whereupon chain conveyor 30 performs its next operating cycle and transports the next ampul 1 into inspection station 10.

In a prototype of inspection station 10, the removal time, for a stroke of 10 mm and a lifting speed of about 200 mm/s, was approximately 100 mm/s once the chain had stopped, while the lowering time was also approximately 100 mm/s. The photodiode camera system 12 had a measuring range of 20 mm with a resolution of 0.01 mm. Per second, 1400 measured values could be picked up. The radial resolution was 0.05 mm. A high pressure mercury vapor lamp having a power of 150 Watt and producing an illuminated surface of 200 × 50 mm was employed as the illumination source 11.

Further details of inspection station 10 are illustrated in FIGS. 6 to 9, which will now be described in greater detail.

Figure 6:
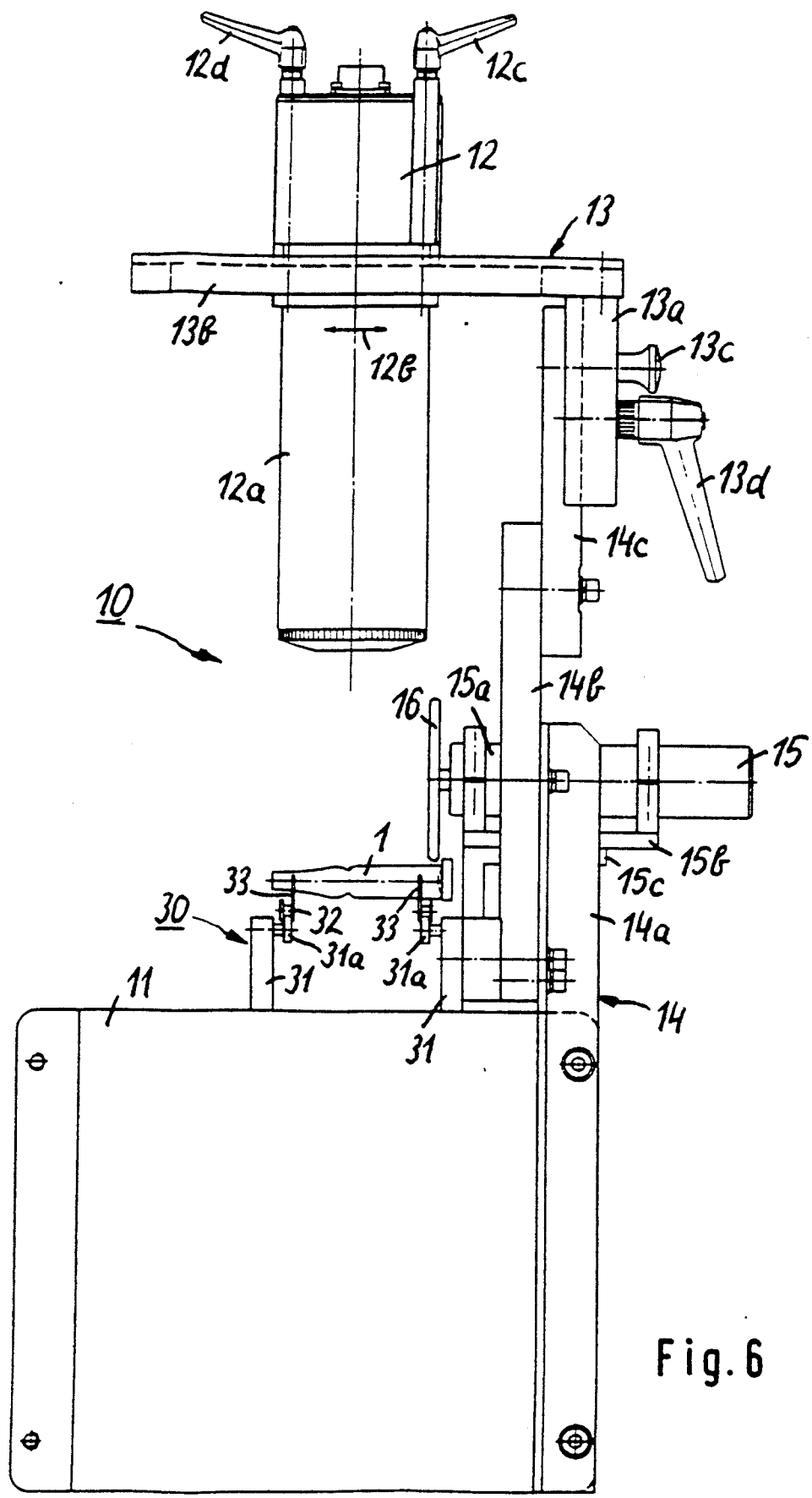
FIG. 6 is a front view of a further inspection station for monitoring the colored marker and the scratch mark on OPC ampuls provided in the device according to FIG. 3.

As shown in FIG. 6, inspection station 10 includes a vertical framework 14 which is composed of a lower support 14a, a portal 14b screwed to its arms and an end plate 14c screwed to the yoke of portal 14b. End plate 14c supports the vertical arms of a transverse member 13 that is configured as a carriage 13a, with photodiode camera system 12 being mounted on the horizontal guide arms 13b of the transverse member so as to be horizontally displaceable in the direction of the double arrow 12b. Carriage 13a rides in part on the side faces of end plate 14c and can be displaced vertically with respect to end plate 14c by means of a handle 13c and can be locked in any vertical position relative to end plate 14c by means of an arresting lever 13. Photodiode camera system 12 also is provided with two oppositely disposed arresting levers 12c and 12d in order to permit locking of camera system 12 in any desired horizontal position. With the aid of the mentioned vertical and horizontal adjustment possibilities, photodiode camera system 12 can be adjusted exactly on an ampul 1 which is being pressed by lifter remover 80, shown in greater detail in FIGS. 7 to 9, against friction wheel 16. The latter is driven by an electric motor 15 by way of an intermediately connected gear mechanism 15a. In the mentioned prototype of inspection station 10, motor 15 had a power of 15 Watt with an applied direct voltage of 24 Volts. Gear mechanism 15a rotated at 100 revolutions per minute with a maximum continuous torque of 115 N/cm. Electric motor 15 and gear mechanism 15a are supported by an auxiliary frame 15b which is attached to support 14a by way of an angular fastening bracket 15c. Electric motor 15 and gear mechanism 15a can be displaced within auxiliary frame 15b in the direction of their longitudinal axis in order to position friction wheel 16 exactly on the cylindrical body 2 (FIG. 1) of the ampul 1 held in lifter remover 80.

Also fastened to support 14a is one guide track 31 of chain conveyor 30 whose second, opposite, guide track 31 is supported in a manner not illustrated. The housing for illumination source 11 lies flush against the underside of the two guide tracks 31 and is itself fastened to support 14a. As already mentioned, in the prototype inspection station 10 the illuminated surface was 200 × 50 mm, with the greater length of 200 mm extending in the axial direction of ampul 1.

On the interior of each guide track 31, in the region of its upper end, a guide rail 31a having a rectangular profile is fastened by way of webs. The chain links 32 of the chain conveyor 30 travel on the guide rails 31a. A small bearing plate 33 is fastened to the interior of each chain link 32, with the free end of the bearing plate being sloped like a roof so that every two adjacent bearing plates 33 form a V-shaped supporting groove for an ampul 1. The above details of chain conveyor 30 are also evident in the enlarged view of FIG. 7.

The lifter remover 80 (FIG. 3) is provided in order to lift ampuls 1 out of their V-shaped supporting groove in chain conveyor 30. Lifter remover 80 is omitted in the view of FIG. 6 and its details will be described in connection with FIGS. 7 to 9. As is evident particularly from FIGS. 8 and 9, lifter remover 80 is provided with two parallel pivot arms 81a and 81b which are mounted so as to pivot in a vertical plane about a pivot bearing 82. Pivot bearing 82 includes two bearing blocks 82a and 82b which flank pivot arms 81a and 81b and support pivot axis 82c. Bearing blocks 82a and 82b in turn are fastened to side members 83a and 83b, respectively, of the lifter remover housing so as to be vertically displaceable. For this purpose, each bearing block 82a and 82b, respectively, is provided with a long hole guide or slot 84 through which passes an adjustment screw 85.

In the region of the left housing end, at a bottom plate 83c, a hydraulic cylinder 86 is mounted whose piston 86a is articulated to the left lever sections of pivot arms 81a and 81b. Piston 86a operates against the force of a tension spring 87 which is connected, on the one hand, with a connecting piece 81c at the ends of pivot arms 81a and 81b and, on the other hand, with the bottom plate 83c. Tension spring 87 pre-tensions pivot arms 81a and 81b counterclockwise.

Figure 7:
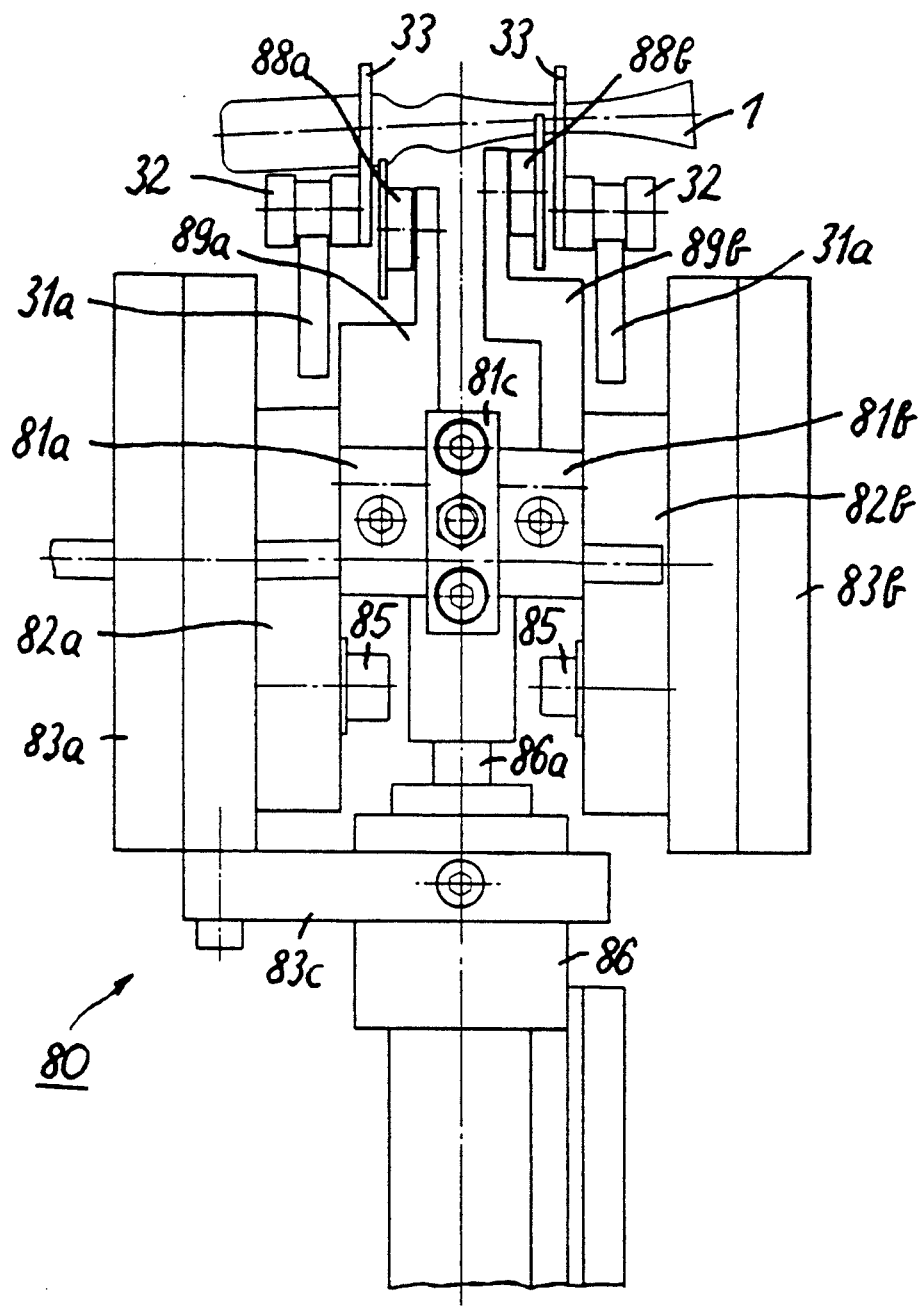
FIG. 7 is a front view of a lifter remover provided in the inspection station of FIG. 6.
Figure 8:
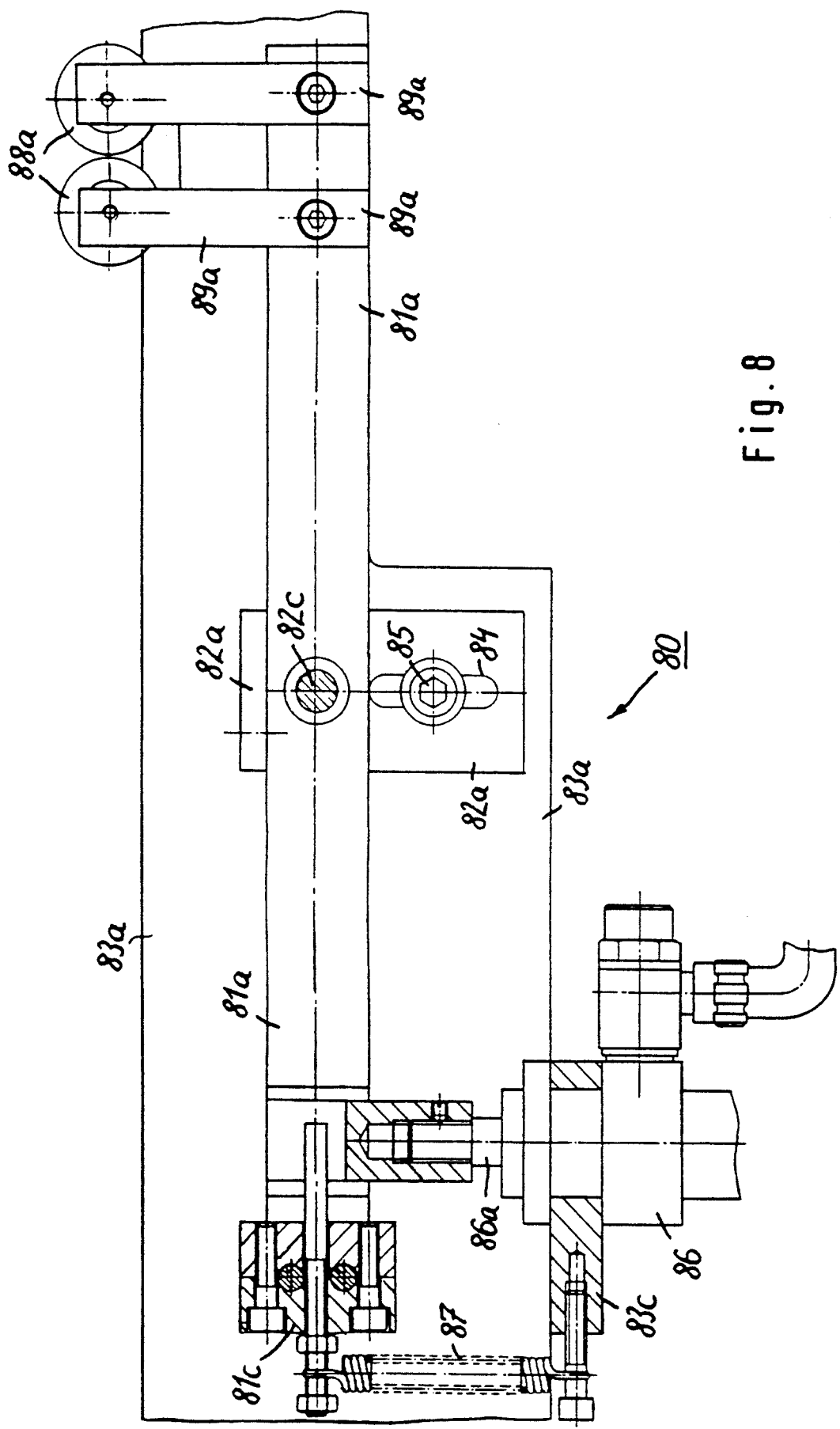
FIG. 8 is a side view of the lifter remover of FIG. 7.

In the region of their right-hand ends (which enter into the inspection station) pivot arms 81a and 81b are each provided with a pair of rollers 88a and 88b, respectively, which form two supporting grooves for the rotatable support of the ampul 1 to be inspected. Each roller pair 88a and 88b is rotatably mounted at two associated bearing blocks 89a and 89b, respectively, which in turn are screwed to the respectively associated pivot arm 81a and 81b. As can be seen in FIG. 7, roller pairs 88a and 88b engage into the space between the bearing plates 33 of chain conveyor 30 so that a counterclockwise pivotal movement of pivot arms 81a and 81b causes the ampul 1 disposed in the V-shaped supporting grooves of bearing plates 33 to be gripped by the two roller pairs 88a and 88b and to be lifted vertically upward (lifter remover 80 in the lifted-out state). For this purpose, hydraulic cylinder 86 is deactivated which causes pivot arms 81a and 81b to be moved counterclockwise under the force of tension spring 87. To lower roller pairs 88a and 88b, hydraulic cylinder 86 is charged with hydraulic pressure, which causes pivot arms 81a and 81b to be turned clockwise against the force of tension spring 87. In the lifted-out state, ampul 1 is rotatably supported, as already mentioned, by each roller pair 88a and 88b so that ampul 1 can be easily rotated by friction wheel 16 (FIG. 6). Tension spring 87 here generates the necessary contact pressure between friction wheel 16 and ampul 1.

Figure 9:
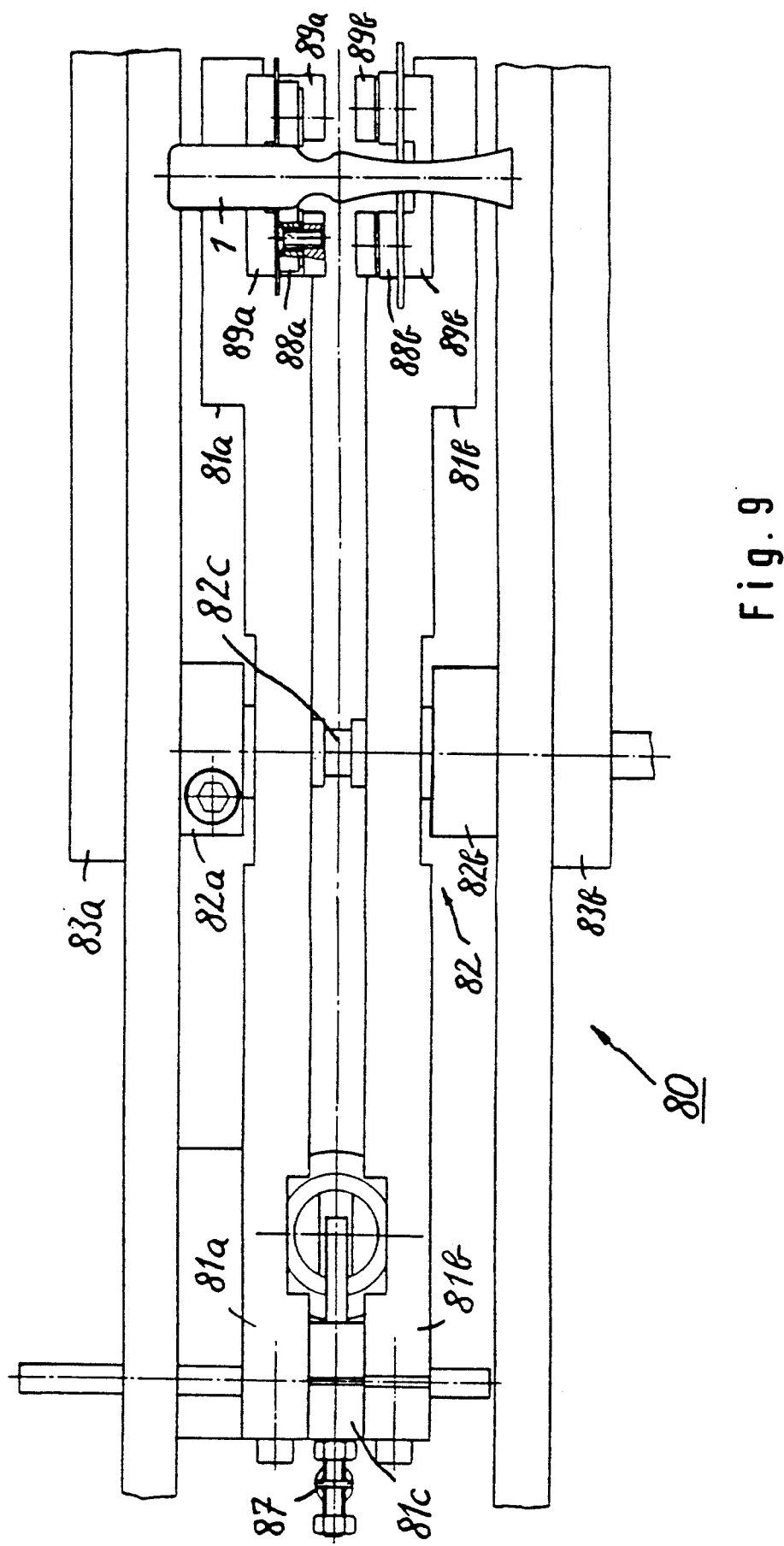
FIG. 9 is a top view of the lifter remover of FIGS. 7 and 8.

As can be seen well in FIG. 9, the right-hand end regions of pivot arms 81a and 81b are provided with step-shaped sections in order to be able to accommodate, on the one hand, bearing blocks 89a and 89b and, on the other hand, impede as little as possible the passage of the diffuse light from illumination source 11 through ampul 1. However, the unavoidable shading by roller pairs 88a and 88b has no adverse influence on the measuring results due to the illumination of ampul 1 with diffuse light. In this connection, it must be considered that the transition region 4 of each OPC ampul (FIG. 1), which is the only part of interest for the examination of the colored marker 5 and the desired break location 5a in inspection station 10, lies in the region between roller pairs 88a and 88b (FIG. 9), so that the transition region 4 of OPC ampul 1 is well illuminated by the illumination from the bottom.

However, for an examination of the entire outline of the ampul, the components of lifter remover 80 would interfere too much with the illumination of ampul 1 from the bottom by illumination source 11. For that reason, an automatic outline check is made in opto-electronic inspection station 20 (FIG. 3), whose structural details will be described below with reference to FIGS. 4 and 5. As this indicates, inspection station 20 includes a vertical framework 28 in which the guide arms 25a of a horizontal transverse member 25 are rigidly fastened to the upper end of the framework. A camera system composed of three photodiode cameras 22, 23 and 24 is mounted so as to be horizontally displaceable on guide arms 25a in the direction of the double arrow 25b. The three photodiode cameras 22 to 24 are arranged one behind the other in such a way that their optical axes 22a, 23a, and 24a, respectively, lie in a common plane which intersects the longitudinal axis of the ampul 1 to be examined. The optical axes 22a, 23a and 24a converge in a point that lies below the ampul 1 to be examined. This means that the optical axis 23a of the photodiode camera 23 in the middle extends vertically and the optical axes 22a and 24a of the two outer photodiode cameras 22 and 24 extend at an angle of inclination of less than 90° with respect to the longitudinal axis of the ampul 1 to be examined.

Figure 4:
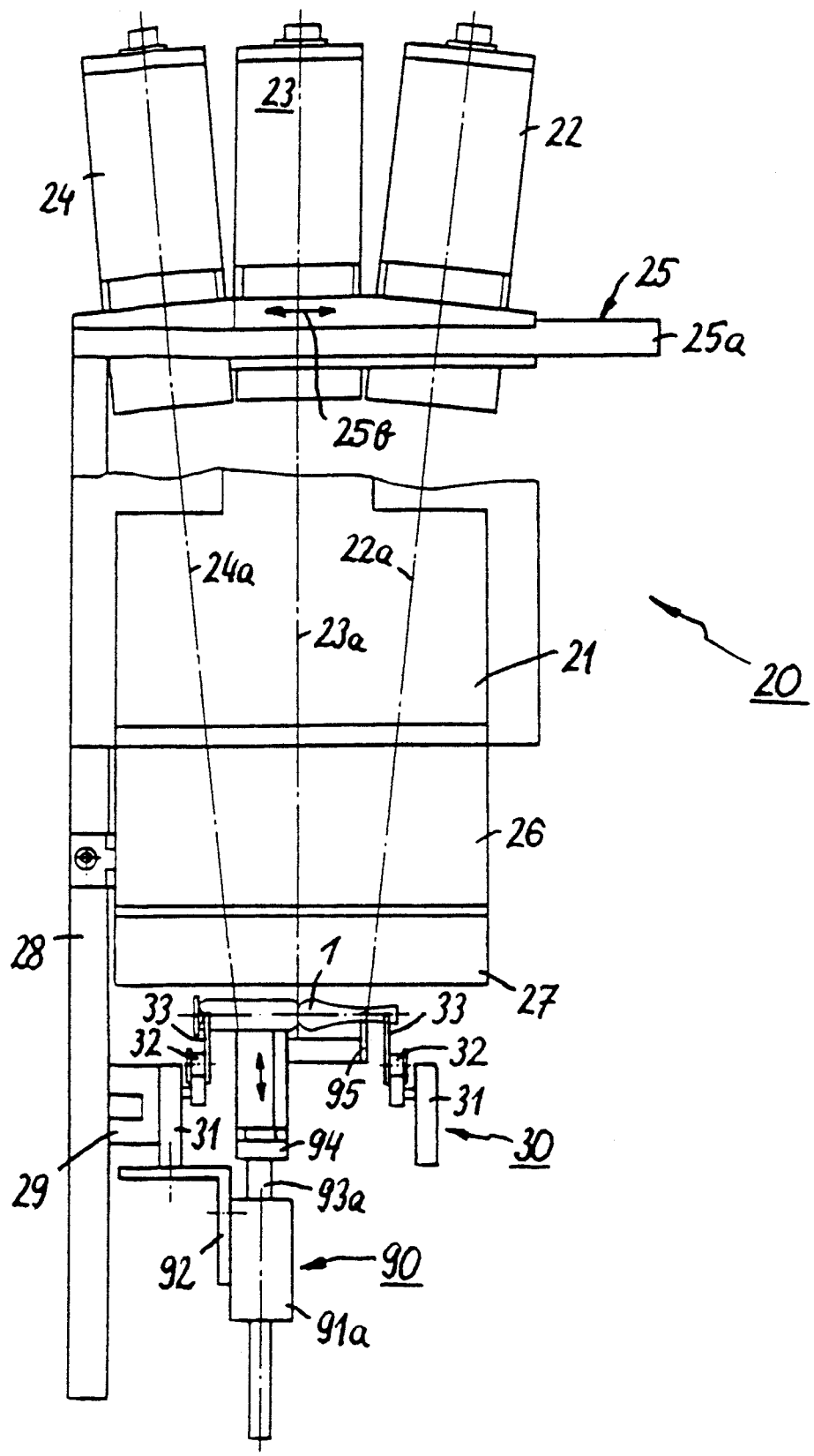
FIG. 4 is a front view of an inspection station for checking outlines as provided in the inspection apparatus of FIG. 3.
Figure 5:
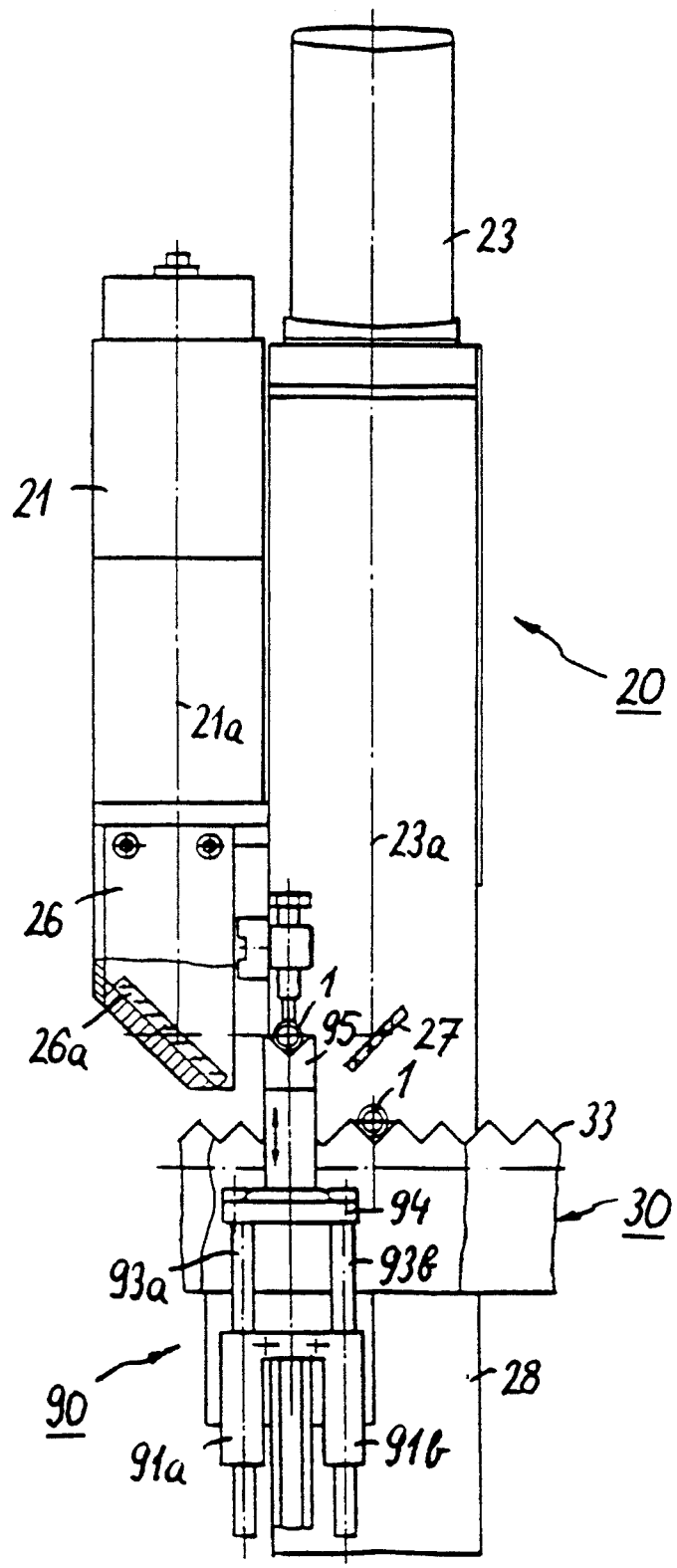
FIG. 5 is a side view of the inspection station of FIG. 4.

Below the ampul 1 to be examined, that is, in the region where illumination source 11 is disposed in inspection station 10, a lifter remover 90 is provided in inspection station 20 and will be described in greater detail below. In order to illuminate ampul 1 with diffuse light, an illumination source 21 is arranged axially parallel and immediately adjacent to the middle photodiode camera 23, as can be seen in FIG. 5. The diffuse light from illumination source 21, which is directed vertically from the top to the bottom, is deflected by way of a 45° mirror 26a onto the ampul 1 to be examined. Deflection mirror 26a is arranged in such a way that the optical axis 21a of illumination source 21, once deflected at mirror 26a, impinges on the longitudinal axis of ampul 1 to be examined at an angle of 90°. For this purpose, deflection mirror 26a is attached to a mirror holder 26 that is fastened to vertical framework 28 (FIG. 4).

The light deflected by deflection mirror 26a onto ampul 1 is able to pass through ampul 1 practically unimpededly since the ampul is supported only in the region of its axial ends in V-shaped bearing notches of two vertical arms 95 of lifter remover 90. The light passing through ampul 1 impinges on a further 45° deflection mirror 27 which is attached in such a way that the optical axis 21a of illumination source 21 which passes perpendicularly through the longitudinal axis of ampul 1 is reflected exactly into the optical axis 23a of the middle photodiode camera 23. The mounting of deflection mirror 27 is not shown in detail in FIGS. 4 and 5. The transmitted light which is reflected at deflection mirror 27 toward photodiode cameras 22, 23, 24 (FIG. 4) contains optical information about the outline of ampul 1. This outline is completely imaged in the form of three overlapping axial sections on the photodiode matrixes of the three photodiode cameras 22, 23 and 24. The use of three successively arranged photodiode cameras 22, 23 and 24 is necessary since a single photodiode camera is able to image only an axial section (for example, of transition region 4 of FIG. 1), as is the case for photodiode camera system 12 of inspection station 10.

Lifter remover 90 includes two parallel operating hydraulic cylinders 91a and 91b (FIG. 5) which are fastened by way of an angular fastening bracket 92 (FIG. 4) to one of the guide track S 31 of chain conveyor 30. This guide track 31 is connected by way of a bracket 29 with the vertical framework 28. The support for the other guide track 31 is not shown in FIG. 4. The pistons 93a and 93b of the two parallel hydraulic cylinders 91a and 91b are connected with one another by means of a common yoke plate 94 which supports arms 95. The arms 95 engage in the space between bearing plates 33 of chain conveyor 30 and, when the hydraulic cylinders 91a, 91b perform their upward stroke, lift the ampul 1 to be examined from its support in the V-shaped support grooves of bearing plates 33 (FIG. 5).

The stroke of hydraulic cylinders 91a and 91b is dimensioned in such a way that, at the end of the lifting movement, the longitudinal axis of the lifted-out ampul 1 is exactly perpendicularly intersected by the deflected optical axis 21a of illumination source 21, as this is shown in FIG. 5.

In a prototype of inspection station 20, the measuring range of the camera system composed of three photodiode cameras had a length of 105 × 50 mm, with the resolution in length being 0.07 mm and the resolution in diameter 0.1 mm. A total of 1.7 ampuls were gripped per second. A halogen illumination source exhibited a power of 20 W at a supplied direct voltage of 12 V, with the illuminated surface having a size of 150 × 40 mm. The lifter remover performed a stroke of 50 mm at a lifting speed of about 200 mm/s with a lifting time of a maximum of 250 ms after the chain had stopped and a lowering time of a maximum of 200 ms.

With the aid of the method according to the invention, medical ampuls from 1 to 30 ml can be measured fully automatically and with respect to all standardized dimensions or features. In particular, the following advantages result:

integration of the measuring system in existing ampul production lines employing chain conveyors;

implementation of entire inspection during the pauses in the production cycle;

fully automatic examination of the intended break locations of OPC ampuls;

fully automatic inspection of outline dimensions pursuant to DIN 58,377;

automatic detection of residual splinters in the ampul body;

automatic sorting out of the reject ampuls;

automatic sorting according to different ampul types ("lance classes" according to FIGS. 2A-2C);

automatic calculation of the size of a sample with separate sorting of the sample;

provision of statistics for total errors;

compilation of an internal error protocol;

compilation of an inspection protocol intended for the end user;

output of a statistical error distribution with machine capability by way of a sample;

automatic program call-up by way of a parts data base, customer data base and article number;

separate operation of the individual inspection stations for OPC ampuls and automatic outline evaluation;

interface for the connection of the measuring system to higher order computer systems;

actuation of operator friendly monitoring and warning devices;

connection of the entire system into an existing control concept for the production line; and simple calibration and examination of system functions.

We claim:

1. A method for inspecting a medical ampul for dimensional accuracy, the ampul having a longitudinal axis, said method comprising the steps of:

(a) conveying the ampul in a horizontal position on a conveying device which moves the ampul in cycles along a path;

(b) lifting the ampul from the conveying device;

(c) illuminating the ampul perpendicular to its longitudinal axis with light from a diffusely radiating illumination source, so that light passes through the ampul and is modulated by the ampul;

(d) detecting the modulated light with a camera system which produces at least one camera signal with information about the configuration of the ampul;

(e) conveying the at least one camera signal to a digital image evaluation unit; and (f) determining the dimensions of the ampul in the digital image evaluation unit.

2. The method of claim 1, wherein the camera system comprises photodiodes, and wherein the modulated light is detected in step (d) by the photodiodes.

3. The method of claim 1, further comprising the step of rotating the ampul about its longitudinal axis while steps (b) and (c) are conducted.

4. The method of claim 1, wherein the ampul is a one-point-cut ampul, wherein the camera system is disposed above the ampul, and wherein step (c) is conducted by shining light upward from an illumination source disposed below the ampul, the illumination source and the camera system being located along a straight line which passes perpendicularly through the longitudinal axis of the ampul.

5. The method of claim 1, wherein the camera system is movably mounted, and further comprising the step of moving the camera system to a predetermined position with respect to the ampul.

6. The method of claim 1, wherein step (b) is conducted by pivoting a lifter remover having roller parts, and further comprising the step of rotating the ampul about its longitudinal axis with a friction wheel while the ampul is supported on the roller pairs.

7. The method of claim 1, wherein the camera system is disposed above the ampul, and therein step (c) comprises the steps of shining light downward from an illumination source that is disposed above the ampul and adjacent the camera system, and reflecting the light from the illumination source by about 90° to illuminate the ampul, and wherein step (d) comprises reflecting the modulated light by about 90° to the camera system.

8. The camera system of claim 7, wherein the camera system comprises a first photodiode camera having a first optical axis, a second photodiode camera having a second optical axis, and a third optical camera having a third optical axis, wherein the photodiode cameras are disposed so that the first, second, and third optical axes lie in a first plane and intersect at an intersection point, the first plane being parallel to the longitudinal axis of the ampul, wherein the second optical axis additionally lies in a second plane that is perpendicular to the first plane and to the longitudinal axis of the ampul, the first and third optical axes being inclined with respect to the second plane, and wherein the step of reflecting the modulated light by about 90° the camera system is conducted using a mirror which is positioned between the photodiode cameras and the intersection point.

9. The method of claim 8, wherein the step of shining the light downward is conducted by shining the light downward along a beam path that is parallel to the first plane.

10. The method of claim 7, wherein the camera system is movably mounted, and further comprising the step of moving the camera system parallel to the longitudinal axis of the ampul.

11. The method of claim 7, wherein step (b) comprises actuating a lifting plunger of a lifter remover to raise two arms of the lifter remover, the arms having V-shaped supporting notches in which the ampul is supported.

12. A method for inspecting a medical ampul for dimensional accuracy, the ampul having a longitudinal axis, said method comprising the steps of:

(a) moving the ampul to a predetermined examination position lying in an optical path which extends between a light source and a camera system, the optical path passing through the ampul perpendicular to its longitudinal axis when the ampul is in the examination position;

(b) conveying signals from the camera system to a digital image evaluation unit; and (c) moving the ampul away from the examination position, wherein step (a) comprises moving the ampul along an ampul path which extends horizontally while the longitudinal axis of the ampul is substantially horizontal, and raising the ampul to the examination position, and wherein step (c) comprises lowering the ampul back to the ampul path.

13. The method of claim 12, further comprising the step of rotating the ampul while it is in the examination position.

14. The method of claim 12, wherein the step of raising the ampul to the examination position comprising pivoting a lifter remover to raise the ampul along an arcuate path.

15. The method of claim 12, wherein the step of raising the ampul to the examination position comprises actuating a lifter remover which raises the ampul along a straight path.

16. The method of claim 12, wherein the examination position is disposed between a pair of mirrors which bend the optical path, and wherein the step of raising the ampul to the examination position is conducted by moving the ampuls between the mirrors.

17. The method of claim 12, wherein the digital image evaluation unit determines ampul dimensions for a plurality of ampul features, compares the ampul dimensions with predetermined values, and identifies any out-of-tolerance ampul features, and further comprising the step of displaying an out-of-tolerance indicator on a display board for every out-of-tolerance ampul feature identified by the digital image evaluation unit, each out-of-tolerance indicator on the display board corresponding to a respective one of the ampul features.

18. A method for inspecting a medical ampul for dimensional accuracy, the ampul having a longitudinal axis, said method comprising the steps of:

(a) moving the ampul to a predetermined examination position lying in an optical path which extends between a light source and a camera system, the optical path passing through the ampul perpendicular to its longitudinal axis when the ampul is in the examination position;

(b) conveying signals from the camera system to a digital image evaluation unit; and (c) moving the ampul away from the examination position;

wherein step (a) comprises moving the ampul away from the light source and toward the camera system.

19. The method of claim 18, wherein step (a) further comprises moving the ampul along an ampul path to a position between the light source and the camera system, wherein the step of moving the ampul away from the light source and toward the camera system is conducted by moving the ampul from the ampul path to the examination position, and wherein step (c) comprises returning the ampul to the ampul path.

20. The method of claim 19, wherein the step of moving the ampul from the ampul path to the examination position is conducted by moving the ampul substantially perpendicularly to the ampul path.

21. The method of claim 18, further comprising the step of rotating the ampul about its longitudinal axis while it is in the examination position.

* * * * *